United States Patent [19]

Fujita et al.

[11] Patent Number: 4,720,551
[45] Date of Patent: Jan. 19, 1988

[54] CHLOROTHIENYL-IMIDAZOLE PROPENONES

[75] Inventors: Takayuki Fujita, Matsushige; Hiroko Yabe; Tadashi Akita, both of Tokushima, all of Japan

[73] Assignee: Shikoku Chemicals Corporation, Kagawa, Japan

[21] Appl. No.: 906,432

[22] Filed: Sep. 12, 1986

[30] Foreign Application Priority Data

Sep. 26, 1985 [JP] Japan ................................. 60-124321
Sep. 26, 1985 [JP] Japan ................................. 60-214322

[51] Int. Cl.$^4$ ......................................... C07D 409/06
[52] U.S. Cl. ................................... 548/336; 548/341
[58] Field of Search ................. 548/336, 341; 514/397, 514/399

[56] References Cited

U.S. PATENT DOCUMENTS 4,182,862 1/1980 Chan ................................. 548/341 X

OTHER PUBLICATIONS

Chemical Abstracts, 87:68368c, (1977)[Ger. Offen. 2,645,617, 4/21/77, Balasubramanyan et al.].
Chemical Abstracts, 92:128915u, (1980)[Jpn. Kokai 79,76,579, 6/19/79, Funaki et al.].
Chemical Abstracts, 95:132907x, (1981)[Ger. Offen. 3,000,643, 7/16/81, Elbe].

March, J., *Advanced Organic Chemistry*, McGraw Hill, New York, 1968, pp. 697–698.

*Primary Examiner*—Richard A. Schwartz
*Attorney, Agent, or Firm*—Sherman and Shalloway

[57] ABSTRACT

Disclosed are compounds represented by the following general formula and its hydrochloride salts:

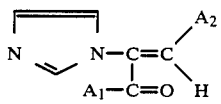

wherein $A_1$ stands for a phenyl group, a halophenyl group, a thienyl group or a halothienyl group, and $A_2$ stands for a phenyl group or a halophenyl group.

These compounds can be obtained by reacting an imidazole compound of the following formula:

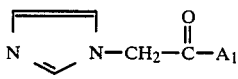

with a benzaldehyde compound of the formula $A_2$-CHO. These compounds are valuable as fungicidal agents.

2 Claims, No Drawings

CHLOROTHIENYL-IMIDAZOLE PROPENONES

BACKGROUND OF THE INVENTION (1) Field of the Invention

The present invention relates to a novel imidazole compound and a process for the preparation thereof.

The compound of the present invention is valuable as an antimildew agent, an antifungal or the like.

(2) Description of the Prior Art

It is known that certain imidazole compounds have a fungicidal action. For example, Japanese Patent Publication No. 16479/68 discloses 1-hydroxy-2-undecyl-3-methylimidazolium-p-toluene-sulfonate, 1-benzyl-2-undecyl-3-methylimidazolium methyl-sulfate and 1-dodecyl-2-ethyl-3-benzylimidazolium chloride as fungicidal agents. Furthermore, the specification of U.S. Pat. No. 4,577,032 discloses 1-benzyldibromomethyl-2-methylimidazole. The compound of the present invention has a much broader antimicrobial spectrum than those of these known compounds.

SUMMARY OF THE INVENTION

In accordance with the present invention, there are provided an imidazole compound represented by the following general formula:

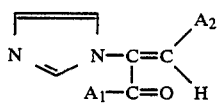  (1)

wherein
$A_1$ stands for a phenyl group, a halophenyl group, a thienyl group or a halothienyl group, and
$A_2$ stands for a phenyl group or a halophenyl group, and an acid addition salt thereof, especially a hydrochloride thereof.

This hydrochloride salt is represented by the following general formula:

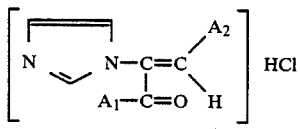  (2)

wherein $A_1$ and $A_2$ are as defined above.

These compounds can be prepared by reacting an imidazole compound represented by the following general formula:

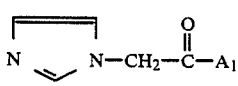  (3)

wherein $A_1$ is as defined above, with a benzaldehyde compound represented by the following general formula:

  (4)

wherein $A_2$ is as defined above.

It is preferred that in the above formula (1), the group $A_1$ be a group represented by the following formula:

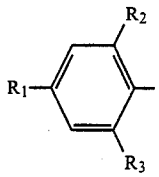  (5)

wherein $R_1$, $R_2$ and $R_3$ each stand for a hydrogen atom or a halogen atom, or a group represented by the following formula:

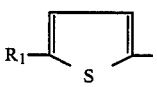  (6)

wherein $R_1$ stands for a hydrogen atom or a halogen atom.

It also is preferred that the group $A_2$ be a group represented by the following formula:

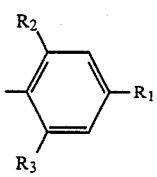  (7)

wherein $R_1$, $R_2$ and $R_3$ each stand for a hydrogen atom or a halogen atom.

DESCRIPTION OF THE INVENTION

The imidazole compound of the formula (3) used as the starting compound in the present invention is obtained by reacting imidazole with a bromoacetophenone compound in dimethylformamide as the solvent (see E. F. Godefroi, J. Med. Chem., 12, page 784 (1969)). The intended compound of the present invention is obtained by adding an equimolar amount of a benzaldehyde compound of the formula (4) to this imidazole compound of the formula (3), heating the mixture in the presence of piperidine in a solvent such as anhydrous benzene at 60° to 80° C., removing the solvent under a reduced pressure, and separating and purifying the intended compound by silica gel column chromatography of the residue or by adding a solvent such as isopropyl ether to the residue to precipitate a crystal and performing recrystallization from a solvent such as ethyl acetate, petroleum ether or acetonitrile.

The intended compound in the form of a hydrochloride salt can be obtained according to the same procedures as described above except that a hydrochloric acid-alcohol solution is added to the above-mentioned residue.

Compounds of the present invention are characterized in that they are in the form of white or yellow crsytals, neutral or weakly acidic, hardly soluble in water and soluble in ethyl acetate, petroleum ether, acetonitrile, isopropanol and ethyl ether.

These compounds have relatively broad antimicrobial spectrum and are valuable as fungicidal agents.

The present invention will now be described in detail with reference to the following examples that by no means limit the scope of the invention.

EXAMPLE 1

Preparation of 1-phenyl-2-(1H-imidazolyl)-3-(2,4-dichlorophenyl)-2-propen-1-one

To a solution of 2.8 g of 2-(1H-imidazolyl)acetophenone and 2.7 g of 2,4-dichlorobenzaldehyde in anhydrous benzene was added 0.5 ml of piperidine, and the mixture was refluxed for 5 hours by using a Dean-Stark trap. The solvent was removed by distillation under a reduced pressure and the residue was washed with petroleum ether two times. Isopropyl ether was added to the residue to precipitate a crystal and the crystal was recrystallized from acetonitrile to obtain 3.4 g of a white crystal having a melting point of 125° to 126° C. From the results of the analysis, it was confirmed that the product was 1-phenyl-2-(1H-imidazolyl)-3-(2,4-dichlorophenyl)-2-propen-1-one having the following structural formula, and the yield was 66%.

(Structural Formula)

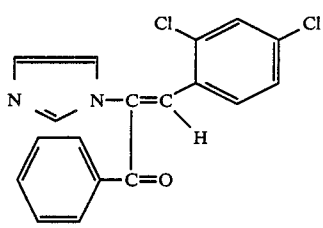

(Analysis Results)

Elementary analysis (as $C_{18}H_{12}N_2OCl_2$, %); Found values: C=62.87, H=3.17, N=7.87; Calculated values: C=62.99, H=3.52, N=8.16.

TLC (chloroform/methanol=10/1) Rf: 0.56.

Infrared absorption spectrum (cm$^{-1}$) 1675 (C=O).

Nuclear magnetic resonance spectroscopy (chloroform-$d_1$, ppm) 6.44–7.89 (12H, m, aromatic, =CH).

EXAMPLE 2

Preparation of 1-(4-chlorophenyl)-2-(1H-imidazolyl)-3-(4-chlorophenyl)-2-propen-1-one To a solution of 3.3 g of 2-(1H-imidazolyl)-4'-chloroacetophenone and 2.7 g of p-chlorobenzaldehyde in anhydrous benzene was added 0.5 ml of piperidine, and the mixture was refluxed for 5 hours by using the Dean-Stark trap. Then, the solvent was removed by distillation under a reduced pressure, and the residue was washed with petroleum ether two times, dissolved in ethyl acetate and cooled by ice to precipitate a crystal. Recrystallization was carried out by using ethyl acetate to obtain 3.6 g of white crystal having a melting point of 129° to 130° C. From the results of the analysis, it was confirmed that the product was 1-(4-chlorophenyl)-2-(1H-imidazolyl)-3-(4-chlorophenyl)-2-propen-1-one having the following structural formula, and the yield was 70%.

(Structural Formula)

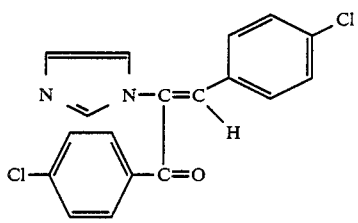

(Analysis Results)

Elementary analysis (as $C_{18}H_{12}N_2OCl_2$, %); Found values: C=63.05, H=3.38, N=7.98. Calculated values: C=62.99, H=3.52, N=8.16.

TLC (chloroform/methanol=10/1) Rf: 0.54.

Infrared absorption spectrum (cm$^{-1}$) 1655 (C=O).

Nuclear magnetic resonance spectroscopy (dimethylsulfoxide-$d_6$, ppm), 6.96 (2H, d, 4- or 5-positions of imidazole), 7.20 (2H, dd, 2-position of imidazole, =CH), 7.57–7.83 (6H, m, aromatic),

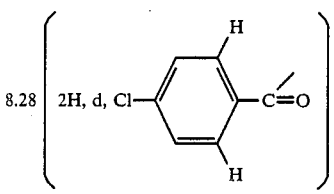

EXAMPLE 3

Preparation of 1-(4-chlorophenyl)-2-(1H-imidazolyl)-3-(2,4-dichlorophenyl)-2-propen-1-one hydrochloride To a solution of 3.3 g of 2-(1H-imidazolyl)-4'-chloroacetophenone and 2.7 g of 2,4-dichlorobenzaldehyde in anhydrous benzene was added 0.5 ml of piperidine, and the mixture was refluxed for 5 hours by using a Dean-Stark trap. The solvent was removed by distillation under a reduced pressure and the residue was washed with petroleum ether two times. A hydrochloric acid-ethanol solution was added to the residue to adjust the pH value to 1, and the mixture was refluxed for 5 minutes, and the solvent was removed by distillation under a reduced pressure and ether was added to the residue to precipitate a crystal. Recrystallization from isopropanol gave 3.8 g of a white crystal having a melting point of 177° to 179° C. From the analysis results, it was found that the product was 1-(4-chlorophenyl)-2-(1H-imidazolyl)-3-(2,4-dichlorophenyl)-2-propen-1-one hydrochloride having the following structural formula, and the yield was 61%.

(Structural Formula)

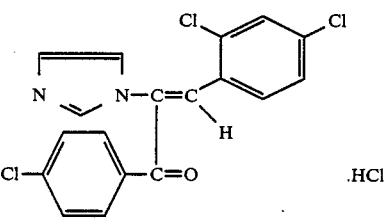

(Analysis Results)

Elementary analysis (as $C_{18}H_{12}N_2OCl_3 \cdot HCl$, %); Found values: C=52.29, H=2.79, N=6.47. Calculated values: C=52.21, H=2.92, N=6.76.

TLC (chloroform/methanol=10/1) Rf: 0.55.

Infrared absorption spectrum (cm$^{-1}$) 1650 (C=O).

Nuclear magnetic resonance spectroscopy (methyl-sulfoxide-d$_6$, ppm), 6.93–7.08 (2H, d, 4- or 5-positions of imidazole), 7.25–7.39 (2H, dd, 2-position of imidazole, =CH), 7.55–7.81 (5H, m, aromatic).

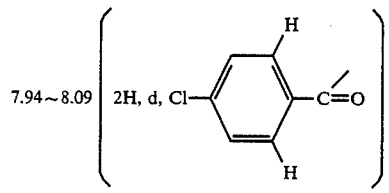

EXAMPLE 4

Preparation of 1-(4-chlorophenyl)-2-(1H-imidazolyl)-3-(2,4-difluorophenyl)-2-propen-1-one To a solution of 2.2 g of 2-(1H-imidazolyl)-chloroacetophenone and 1.5 g of 2,4-difluorobenzaldehyde in 80 ml of anhydrous benzene was added 0.2 ml of piperidine, and the mixture was refluxed for 5 hours by using a Dean-stark trap. The solvent was removed by distillation under reduced pressure, and the residue was separated and purified by silica gel column chromatography (ethyl acetate/n-hexane=2/1). Recrystallization from ethyl acetate and n-hexane gave 1.1 g of a white crystal having a melting point of 105° to 106° C. From the analysis results, it was found that the product was 1-(4-chlorophenyl)-2-(1H-imidazolyl)-3-(2,4-difluorophenyl)-2-propen-1-one having the following structural formula, and the yield was 32%.

(Structural Formula)

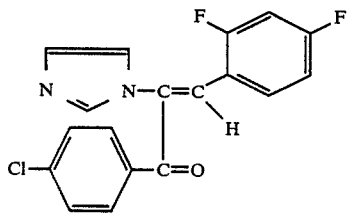

(Analysis Results)

Elementary analysis (as $C_{18}H_{11}N_2OF_2Cl$, %); Found values: C=62.44, H=3.37, N=8.09. Calculated values: C=62.71, H=3.22, N=8.13.

TLC Rf: 0.74 (ethyl acetate/n-hexane=2/1). Rf: 0.68 (chloroform/methanol=10/1).

EXAMPLE 5

Preparation of 1-(4-bromophenyl)-2-(1H-imidazolyl)-3-(2,4-dichlorophenyl)-2-propen-1-one hydrochloride To a solution of 2.7 g of 2-(1H-imidazolyl)-4-bromoacetophenone and 1.8 g of 2,4-dichlorobenzaldehyde in 80 ml of anhydrous benzene was added 0.2 ml of piperidine, and the mixture was refluxed for 7 hours by using a Dean-Stark trap. The solvent was removed by distillation under a reduced pressure and hydrochloric acid-methanol solution was added to the residue to dissolve. The solvent was removed by distillation under a reduced pressure and ether and ethyl acetate were added to the residue to effect crystallization. Recrystallization from ethanol gave 2.2 g of a white crystal having a melting point of 196° to 198° C. From the analysis results, it was found that the product was 1-(4-bromophenyl)-2-(1H-imidazolyl)-3-(2,4-dichlorophenyl)-2-propen-1-one hydrochloride having the following structural formula, and the yield was 47%.

(Structural Formula)

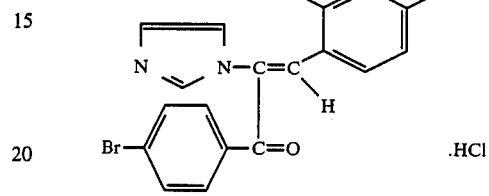

(Analysis Results)

Elementary analysis (as $C_{18}H_{11}N_2OCl_2Br \cdot HCl$, %); Found values: C=46.85, H=2.59, N=5.84. Calculated values: C=47.15, H=2.63, N=6.11.

TLC Rf: 0.80 (ethyl acetate/acetone=5/1). Rf: 0.76 (chloroform/methanol=10/1).

EXAMPLE 6

Preparation of 1-(5-chlorothien-2-yl)-2-(1H-imidazolyl)-3-(2,4-dichlorophenyl)-2-propen-1-one To a solution of 3.4 g of 1-(5-chlorothien-2-yl)-2-(1H-imidazolyl)ethanone and 2.7 g of 2,4-dichlorobenzaldehyde in 80 ml of anhydrous benzene was 0.2 ml of piperidine, and the mixture was refluxed for 7 hours by using Dean-Stark trap. The solvent was removed by distillation under a reduced pressure and the residue was separated and purified by silica gel chromatography (chloroform/methanol=20/1). Recrystallization from ethyl acetate and isopropyl ether gave 2.1 g of a white crystal having a melting point of 110° to 111° C. From the analysis results, it was found that the product was 1-(5-chlorothien-2-yl)-2-(1H-imidazolyl)-3-(2,4-dichlorophenyl)-2-propen-1-one having the following structural formula, and the yield was 37%.

(Structural Formula)

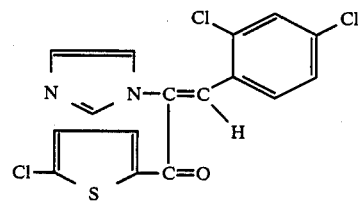

(Analysis Results)

Elementary analysis (as $C_{16}H_9N_2OSCl_3$, %); Found values: C=50.19, H=2.15, N=7.61. Calculated values: C=50.09, H=2.36, N=7.30.

TLC RF: 0.79 (ethyl acetate/acetone=5/1). Rf: 0.80 (chloroform/methanol=10/1).

EXAMPLE 7

Preparation of 1-(5-chlorothien-2-yl)-2-(1H-imidazolyl)-3-(4-chlorophenyl)-2-propen-1-one To a solution of 3.4 g of 1-(5-chlorothien-2-yl)-2-(1H-imidazolyl)ethanone and 2.1 g of 4-chlorobenzaldehyde in 80 ml of anhydrous benzene was added 0.2 ml of piperidine, and the mixture was refluxed for 6 hours by using a Dean-Stark trap. The solvent was removed by distillation under a reduced pressure and ethyl acetate and isopropyl ether were added to the residue to effect crystallization. Recrystallization from ethyl acetate gave 1.7 g of a yellow crystal having a melting point of 137° to 138° C. From the analysis results, it was found that the product was 1-(5-chlorothien-2yl)-2-(1H-imidazolyl)-3-(4-chlorophenyl)-2-propen-1-one having the following structural formula, and the yield was 32%.

(Structural Formula)

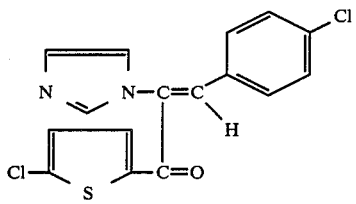

(Analysis Results)

Elementary analysis (as $C_{16}H_{10}N_2OSCl_2$, %); Found values: C=55.30, H=2.66, N=8.29. Calculated values: C=55.03, H=2.89, N=8.02.

TLC Rf: 0.80 (ethyl acetate/acetone=5/1). Rf: 0.79 (chloroform/methanol=10/1).

EXAMPLES 8 THROUGH 30

Imidazole compounds represented by the following structural formula:

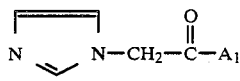

were reacted with benzaldehyde compound represented by the following structural formula:

$A_2$—CHO in the same manner as described in the foregoing examples to prepare compounds represented by the following structural formula:

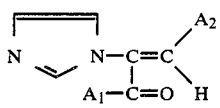

or hydrochlorides thereof. The properties of these compounds were examined. The obtained results are shown in Table 1.

TABLE 1

| Example No. | $A_1$ | $A_2$ | Elementary Analysis Values (%) (calculated values) | | | Melting Point (°C.) | Infrared Absorption Spectrum (C=O, cm$^{-1}$) |
|---|---|---|---|---|---|---|---|
| | | | C | H | N | | |
| 8 | Cl—⟨phenyl⟩— | Cl-⟨phenyl⟩- (o) | 63.21 (62.99) | 3.19 (3.52) | 7.88 (8.16) | 150–151 | 1650 |
| 9 | ⟨phenyl⟩— | ⟨phenyl⟩— | 79.23 (78.81) | 4.97 (5.14) | 10.19 (10.21) | 114.5–115.5 | 1645 |
| 10 | ⟨phenyl⟩— | Cl-⟨phenyl⟩- (o) | 70.15 (70.02) | 4.13 (4.24) | 9.09 (9.07) | 110–111.5 | 1650 |
| 11 | ⟨phenyl⟩— | Cl-⟨phenyl⟩- (p) | 70.26 (70.02) | 4.00 (4.24) | 8.82 (9.07) | 78–79 | 1650 |
| 12 | Cl-⟨phenyl⟩- (o) | ⟨phenyl⟩— | 70.12 (70.02) | 4.01 (4.24) | 9.01 (9.07) | 145–146 | 1665 |
| 13 | Cl-⟨phenyl⟩- (o) | Cl-⟨phenyl⟩- (o) | 63.23 (62.99) | 3.35 (3.52) | 7.82 (8.16) | 103–105 | 1665 |

TABLE 1-continued

| Example No. | A₁ | A₂ | Elementary Analysis Values (%) (calculated values) ||| Melting Point (°C.) | Infrared Absorption Spectrum (C=O, cm⁻¹) |
|---|---|---|---|---|---|---|---|
| | | | C | H | N | | |
| 14 | 2-Cl-phenyl | 4-Cl-phenyl | 62.92 (62.99) | 3.26 (3.52) | 8.10 (8.16) | 128–129 | 1670 |
| 15 | 2-Cl-phenyl | 2,4-diCl-phenyl | 57.28 (57.25) | 2.87 (2.94) | 6.89 (7.42) | 120.5–122 | 1675 |
| 16 | 4-Cl-phenyl | phenyl | 70.30 (70.02) | 4.11 (4.24) | 9.04 (9.07) | 153.5–155 | 1655 |
| 17 | 3,4-diCl-phenyl | phenyl | 62.74 (62.99) | 3.36 (3.52) | 7.87 (8.16) | 81–83 | 1660 |
| 18 | 3,4-diCl-phenyl | 2-Cl-phenyl | 52.30 (52.21) | 3.23 (2.92) | 6.24 (6.76) | 175–177 | 1675 |
| 19 | 3,4-diCl-phenyl | 4-Cl-phenyl | 52.08 (52.21) | 2.78 (2.92) | 6.51 (6.76) | 167–174 | 1670 |
| 20 | 3,4-diCl-phenyl | 2,4-diCl-phenyl | 53.03 (52.46) | 2.61 (2.45) | 6.94 (6.80) | 133–135 | 1675 |
| 21 | phenyl | 4-Br-phenyl | 63.88 (64.10) | 4.02 (3.88) | 7.99 (8.31) | 162–167 | 1655 |
| 22 | 4-Cl-phenyl | 4-Br-phenyl | 56.02 (55.76) | 3.30 (3.12) | 7.01 (7.22) | 135.5–136.5 | 1655 |
| 23 | 4-Br-phenyl | 4-Br-phenyl | 50.15 (50.03) | 2.68 (2.80) | 6.32 (6.48) | 158–159 | 1650 |
| 24 | 4-Br-phenyl | 4-Cl-phenyl | 55.90 (55.76) | 3.05 (3.12) | 6.71 (7.22) | 151–152 | 1650 |

TABLE 1-continued

| Example No. | A₁ | A₂ | Elementary Analysis Values (%) (calculated values) | | | Melting Point (°C.) | Infrared Absorption Spectrum (C=O, cm⁻¹) |
|---|---|---|---|---|---|---|---|
| | | | C | H | N | | |
| 25 | 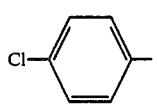 | 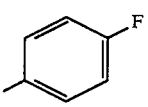 | 66.15 (66.16) | 3.48 (3.70) | 8.81 (8.57) | 124–125 | 1655 |
| 26 | 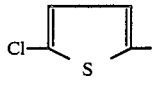 | 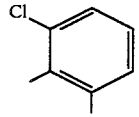 | 50.25 (50.09) | 2.04 (2.36) | 6.93 (7.30) | 111–113 | 1670 |
| 27 | 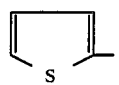 | 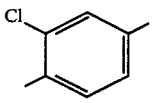 | 55.20 (55.03) | 2.65 (2.89) | 7.93 (8.02) | 137–139 | 1675 |
| 28 | 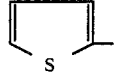 | 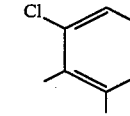 | 55.04 (55.03) | 2.80 (2.89) | 7.87 (8.02) | 117–118.5 | 1675 |
| 29 | 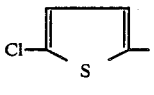 | 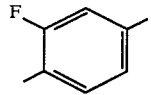 | 55.34 (54.79) | 2.56 (2.59) | 7.83 (7.99) | 117–118 | 1670 |
| 30 | 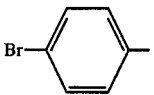 | 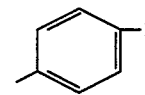 | 58.53 (58.24) | 3.20 (3.26) | 7.48 (7.55) | 144.5–145.5 | 1650 |

Note

The products obtained in Examples 18 and 19 are hydrochloride salts.

EXAMPLE 31

With respect to the compounds obtained in the foregoing examples, the minimum growth inhibiting concentrations to pathogenic bacteria were measured. The obtained results are shown in Table 2. The unit of each value in Table 2 is μg/ml. The used phthogenic bacteria were *Candida albicans, Trichophyton rubrum, Trichophyton mentagrophytes, Trichophyton tonsurans* and *Microsporum gypseum*. Culturing was conducted in Sabouraud's agar culture medium at 25° C. The growth of the bacterium was checked at intervals of 24 hours after inoculation. The minimum concentration at which no colony was measured as the minimum inhibitory concentration after the passage of 7 days.

TABLE 2

| Compound of Present Invention | Candida albicans | Trichophyton rubrum | Trichophyton mentagrophytes | Trichophyton tonsurans | Microsporum gypseum |
|---|---|---|---|---|---|
| Example 1 | <10 | <2.5 | <5 | <2.5 | <2.5 |
| Example 2 | <10 | <1.25 | <2.5 | <2.5 | <2.5 |
| Example 3 | <6.25 | <1.25 | <1.25 | <1.25 | <1.25 |
| Example 4 | <25 | <3.125 | <6.25 | <0.782 | <6.25 |
| Example 5 | <12.5 | <3.125 | <6.25 | <0.782 | <25 |
| Example 6 | 50 | <1.563 | <25 | <1.563 | 50 |
| Example 7 | 25 | <1.563 | <1.563 | <0.782 | <6.25 |
| Example 8 | <25 | <2.5 | <5 | <5 | <2.5 |
| Example 9 | 20 | <10 | <20 | <20 | 20 |
| Example 10 | 20 | <5 | <10 | <10 | <5 |
| Example 11 | 20 | <5 | <10 | <5 | <5 |
| Example 14 | <50 | <25 | <50 | <25 | <25 |
| Example 15 | 20 | <20 | 20 | <20 | <20 |
| Example 16 | 20 | <5 | <20 | <5 | <10 |
| Example 18 | 20 | <20 | 20 | <20 | 20 |
| Example 21 | 50 | <3.125 | <12.5 | <2.5 | <3.125 |
| Example 22 | 50 | <2.5 | <25 | <6.25 | <3.125 |
| Example 23 | <25 | <12.5 | <12.5 | <3.125 | <3.125 |
| Example 24 | <6.25 | <1.56 | <12.5 | <0.391 | <12.5 |
| Example 25 | 50 | <6.25 | <12.5 | <3.125 | <50 |

TABLE 2-continued

| Compound of Present Invention | Candida albicans | Trichophyton rubrum | Trichophyton mentagrophytes | Trichophyton tonsurans | Microsporum gypseum |
|---|---|---|---|---|---|
| Example 26 | <25 | <6.25 | 25 | <6.25 | <25 |
| Example 27 | 25 | <3.125 | <3.125 | <1.56 | <12.5 |
| Example 28 | 25 | <12.5 | 25 | <12.5 | 25 |
| Example 29 | <25 | <12.5 | <25 | <3.125 | <6.25 |
| Example 30 | <25 | <12.5 | <12.5 | <3.125 | <25 |

We claim:
1. 1-(5-Chlorothien-2-yl)-2-(1H-imidazolyl)-3-(2,4-dichlorophenyl)-2-propen-1-one.

2. 1-(5-Chlorothien-2-yl)-2-(1H-imidazolyl)-3-(4-chlorophenyl)-2-propen-1-one.

* * * * *

UNITED STATES PATENT AND TRADEMARK OFFICE
CERTIFICATE OF CORRECTION

PATENT NO. : 4,720,551
DATED : January 19, 1988
INVENTOR(S) : TAKAYUKI FUJITA, HIROKO YABE and TADASHI AKITA It is certified that error appears in the above-identified patent and that said Letters Patent is hereby corrected as shown below:

Title Page, under Foreign Application Priority Data,

"60-124321" should read --60-214321--.

Signed and Sealed this

Seventeenth Day of May, 1988

Attest:

DONALD J. QUIGG

*Attesting Officer*   *Commissioner of Patents and Trademarks*